United States Patent
Oguchi et al.

(10) Patent No.: US 7,038,069 B2
(45) Date of Patent: May 2, 2006

(54) PROCESS FOR OXIDIZING CARBON-CARBON DOUBLE BOND AND PROCESS FOR PRODUCING OXIDIZED COMPOUNDS

(75) Inventors: Wataru Oguchi, Oita (JP); Makoto Nishi, Oita (JP); Yukiharu Hetsugi, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/333,350

(22) PCT Filed: Dec. 24, 2002

(86) PCT No.: PCT/JP02/13447

§ 371 (c)(1),
(2), (4) Date: Jul. 23, 2003

(87) PCT Pub. No.: WO2004/058737

PCT Pub. Date: Jul. 15, 2004

(65) Prior Publication Data

US 2004/0122243 A1    Jun. 24, 2004

(51) Int. Cl.
*C07D 301/03*    (2006.01)
(52) U.S. Cl. ..................................... 549/523
(58) Field of Classification Search ................. 549/523
See application file for complete search history.

(56) References Cited

U.S. PATENT DOCUMENTS 5,262,550 A * 11/1993 Crocco et al. ............. 549/531
2003/0040649 A1    2/2003 Oguchi et al.

FOREIGN PATENT DOCUMENTS

| JP | 6-9592 A | 1/1994 |
|---|---|---|
| JP | 11-165074 | 6/1999 |
| JP | 2001-106680 A | 4/2001 |
| JP | 2001-233867 | 8/2001 |
| JP | 2002-102709 | 4/2002 |

* cited by examiner

*Primary Examiner*—Amelia A. Owens
(74) *Attorney, Agent, or Firm*—Sughrue Mion, PLLC

(57) ABSTRACT

A method of oxidizing a carbon-carbon double bond wherein the compound having the carbon-carbon double bond is suppressed, the unreacted compound is separated from the reaction product, and thereafter the thus obtained unreacted compound is again used for the oxidizing reaction; and a process for producing an oxidized compound utilizing such an oxidizing method. When this method is used, an intended oxidized compound can be obtained with high selectivity and high productivity.

9 Claims, 1 Drawing Sheet

PROCESS FOR OXIDIZING CARBON-CARBON DOUBLE BOND AND PROCESS FOR PRODUCING OXIDIZED COMPOUNDS

TECHNICAL FIELD

The present invention relates to a method of oxidizing a carbon-carbon double bond of a compound having at least two or more functional groups with at least one functional group being a carbon-carbon double bond (hereinafter, sometimes simply referred to as "Compound A"), using a titanosilicate catalyst, and a process for producing an oxidized compound utilizing such an oxidizing method.

More specifically, the present invention relates to a method of oxidizing a carbon-carbon double bond of Compound A, wherein the oxidizing reaction of the carbon-carbon double bond of Compound A is highly selectively performed by using a peroxide as an oxidizing agent, in the presence of a titanosilicate catalyst, and also relates to a process for producing an oxidized compound (preferably an epoxy compound) utilizing the oxidizing method.

BACKGROUND ART

In general, "zeolite" has been used as a generic term for crystalline and porous aluminosilicates, and the basic unit of the structure of the "zeolite" has been $(SiO_4)^{4-}$ or $(AlO_4)^{5-}$ having a tetrahedral structure. However, it has recently been clarified that a structure peculiar to or analogous to such a "zeolite" is also present in many other oxides such as aluminophosphate.

In addition, the International Zeolite Association (hereinafter, simply referred to as "IZA") summarizes the definition of the zeolite in W. Meier, D. H. Meier, D. H. Olxon and Ch. Baerlocher, *Atlas of Zeolite Structure Types*, 4$^{th}$ Edition, Elsevier (1996) (hereinafter, simply referred to as the "Atlas"). According to this Atlas, substances having a similar structure other than aluminosilicate, are described as an object substance in prescribing the structure, and these substances are called as a "zeolite-like material" in the Atlas (With respect to the details of the history concerning this definition, Yoshio Ono and Takeaki Yajima, *Zeolite no Kagaku to Kogaku* (*Science and Engineering of Zeolites*), pp. 1–2, published by Kodansha (Jul. 10, 2000) may be referred to).

In the present specification, the definition of "zeolite" follows the above definition as described in Yoshio Ono and Takeaki Yajima, *Zeolite no Kagaku to Kogaku* (*Science and Engineering of Zeolites*), pp. 1–2, published by Kodansha (Jul. 10, 2000), where the term "zeolite" may include not only aluminosilicates but also substances (such as titanosilicate) having a structure analogous to the aluminosilicate.

In the present specification, the structures of zeolite and zeolite-like materials are denoted by a structural code using three alphabetic capital letters approved by IZA and originated in the standard substance which has first been used for the clarification of the structure thereof. The structural codes include those contained in Atlas and those approved in the 4$^{th}$ edition, et seq.

In the present specification, the terms "aluminosilicate" and "titanosilicate" are not limited at all by the properties and/or states thereof (such as crystalline or amorphous, or porous or not porous). Therefore, in the present specification, these terms denote "aluminosilicates" and "titanosilicates" of all properties, unless otherwise indicated specifically.

In the present specification, the term "molecular sieve" means an activity or operation for classifying the molecules by the size thereof, and the term also means a substance having such a function. Zeolite is also included in the definition of this molecular sieve (With respect to the details thereon, the portion relating to "molecular sieve" in *Hyojun Kagaku Yogo Jiten* (*Standard Chemical Glossary*), edited by the Chemical Society of Japan, published by Maruzen (Mar. 30, 1991) may be referred to).

The "meso-porous body" as used in the present specification is a porous substance having a pore size of 2 to 50 nm (With respect to the details thereon, Yoshio Ono and Tateaki Yajima (compilers), *Zeolite no Kagaku to Kogaku* (*Science and Engineering of Zeolite*), pp. 13–23, Kodansha (Jul. 10, 2000) may be referred to).

After the method of synthesizing "TS-1", which is a zeolite was disclosed in U.S. Pat. No. 4,410,501, various studies have been made on the oxidizing reactions of organic compounds using titanosilicates as the catalyst and peroxides as the oxidizing agent. Specific examples thereof include a method disclosed in JP-A7-242649 (the term "JP-A" as used herein means an "unexamined Japanese patent publication") where olefin compounds are epoxidized by using a crystalline titanosilicate-containing molecular sieve having a structure similar to zeolite beta having a crystal structure code of *BEA and containing no aluminum, as the catalyst, and using hydrogen peroxide or an organic peroxide as the oxidizing agent.

In the oxidizing reaction of compounds having a carbon-carbon double bond such as an olefin compound, using a titanosilicate catalyst, a ring-opening reaction of the epoxy group is liable to occur on the resultant product of the epoxy compound and, as a result, the selectivity of the epoxy compound is disadvantageously decreased. Further, as the catalytic activity decreasing rate is large in such a reaction, the catalyst must be used in a large amount, or the catalyst must be regenerated very often. Thus, it is difficult in many cases to industrially use the titanosilicate catalyst.

On the other hand, JP-A-10-25285 discloses a method wherein a mixture of alcohol and ketone is co-present in the reaction for epoxidizing an olefin compound with hydrogen peroxide by using a crystalline titanosilicate (TS-1) catalyst having a structure code of ZSM-5.

The addition of the mixture of alcohol and ketone was conducted because, in the oxidizing reaction of an olefin compound using hydrogen peroxide as the oxidizing agent, such an addition had been expected to provide an effect of preventing the production of diol as a by-product due to the ring-opening reaction of the epoxy compound (which proceeds mainly in an aqueous phase). Actually, the above-mentioned patent publication describes an example where the catalytic activity is improved by the addition of the mixture of alcohol and ketone. However, this method has a problem that the solvolysis of an epoxy compound with an alcohol or ketone compound occurs to reduce the selectivity of the epoxide compound and, further, the carbonyl compound such as ketone readily produces an explosive organic peroxide as a by-product.

On the other hand, JP-A-11-171880 discloses a method wherein the reaction system is irradiated with ultrasound and ammonium carbonate is used as the co-catalyst in the epoxidation of an allyl halide with a titanosilicate catalyst and hydrogen peroxide. In the specification of this patent publication, there is described an example wherein when the reaction is performed while being irradiated with ultrasound in the co-presence of ammonium carbonate, the ring-opening reaction of the epoxy compound can be suppressed.

However, the ammonium carbonate must be added in a large amount, and the recovery of ammonium carbonate is difficult. Thus, it is problematic to use this method industrially. Further, when ultrasound is irradiated, the catalyst is seriously pulverized into fine powder and it becomes more difficult to separate the catalyst from the reaction mixture and to recover the catalyst.

As described above, although various proposals have been made regarding the oxidizing reaction of an olefin compound using a titanosilicate as the catalyst and a peroxide as the oxidizing agent, the industrially practicable technique is rather limited, and it has not been reported that an intended oxidized compound is obtained with high selectivity by using a simple and easy method in the oxidizing reaction of a carbon-carbon double bond of Compound A.

DISCLOSURE OF INVENTION

An object of the present invention is to provide a method of oxidizing a carbon-carbon double bond of Compound A, where an intended oxidized compound can be obtained with high selectivity and high productivity in a selective oxidizing reaction of a carbon-carbon double bond of Compound A using a peroxide as the oxidizing agent in the presence of a titanosilicate catalyst, and to provide a process for producing an oxidized compound of Compound A by using such an oxidizing method.

As a result of earnest study, the present inventors have found that in the case of an oxidizing reaction of a carbon-carbon double bond of Compound A using a peroxide as the oxidizing agent in the presence of a titanosilicate catalyst, it is extremely effective in attaining the above object to suppress the conversion of Compound A to a certain degree and to again use at least a portion of the unreacted Compound A (which has been separated from the reaction product) in the oxidation reaction so as to prevent the loss of Compound A; and as a result, the intended oxidizing reaction can be performed more efficiently with high selectivity.

More specifically, the present invention (I) is a method of oxidizing a carbon-carbon double bond of Compound A, comprising the following first to third steps:

First Step:
a step of oxidizing a carbon-carbon double bond of Compound A using a peroxide as an oxidizing agent in the presence of a titanosilicate catalyst at a conversion of Compound A of 50 mol % or less to obtain an oxidation reaction mixture;

Second Step:
a step of separating Compound A from the oxidation reaction mixture obtained in the first step; and Third Step:
a step of returning Compound A obtained in the second step to the first step.

In addition, the present invention may include the following matters:

[1] A method of oxidizing a carbon-carbon double bond of a compound at least having two or more functional groups with at least one functional group being a carbon-carbon double bond (hereinafter, sometimes simply referred to as "Compound A"); the oxidizing method comprising the following first to third steps:

First Step:
a step of oxidizing a carbon-carbon double bond of Compound A using a peroxide as an oxidizing agent in the presence of a titanosilicate catalyst at a conversion of Compound A of 50 mol % or less to obtain an oxidation reaction mixture;

Second Step:
a step of separating Compound A from the oxidation reaction mixture obtained in the first step; and Third Step:
a step of returning Compound A obtained in the second step to the first step.

[2] A method of oxidizing a carbon-carbon double bond of Compound A as described in the above [1], wherein the conversion of Compound A in the first step is 30 mol % or less.

[3] A method of oxidizing a carbon-carbon double bond of Compound A as described in the above [1], wherein the conversion of Compound A in the first step is 15 mol % or less.

[4] A method of oxidizing a carbon-carbon double bond of Compound A as described in any one of the above [1] to [3], wherein the peroxide in the first step is a limiting reaction component, the peroxide concentration in the raw material mixture is from 0 to 50% by mass and the conversion of the peroxide is from 30 to 100 mol %.

[5] A method of oxidizing a carbon-carbon double bond of Compound A as described in the above [4], wherein the conversion of the peroxide is from 80 to 100 mol %.

[6] A method of oxidizing a carbon-carbon double bond of Compound A as described in any one of the above [1] to [5], wherein the titanosilicate catalyst is at least one member selected from the group consisting of crystalline titanosilicate and meso-porous titanosilicate.

[7] A method of oxidizing a carbon-carbon double bond of Compound A as described in the above [6], wherein the crystal structure of the crystalline titanosilicate is at least one member selected from the group consisting of MFI-type, AEL-type, EUO-type, FER-type, MEL-type, AFI-type, MWW-type, ATO-type, *BEA-type, MOR-type and -CLO-type, and the composition thereof is represented by the following compositional formula (1):

$$x\text{TiO}_2\cdot(1-x)\text{SiO}_2 \qquad \text{Compositional Formula (1)}$$

(wherein x is from 0.0001 to 0.2).

[8] A method of oxidizing a carbon-carbon double bond of Compound A as described in any one of the above [1] to [7], wherein the oxidizing agent is at least one compound selected from the group consisting of hydrogen peroxide, tert-butyl hydroperoxide, tert-amyl hydroperoxide, cumene hydroperoxide, ethylbenzene hydroperoxide, cyclohexyl hydroperoxide, methylcyclohexyl hydroperoxide, isobutylbenzene hydroperoxide, ethylnaphthalene hydroperoxide and peracetic acid.

[9] A method of oxidizing a carbon-carbon double bond of Compound A as described in any one of the above [1] to [8], wherein the functional group other than the carbon-carbon double bond in Compound A in the first step is at least one functional group selected from the group consisting of an alkenyl group, an alkynyl group, an aryl group, an arene group, an alcohol group, a phenol group, an ether group, an epoxide group, a halogen atom, a carbonyl group, an amido group, a cyanate group, an isocyanate group, a thiocyanate group, an amino group, a diazo group, a nitro group, a nitrile group, a nitroso group, a sulfide group, a sulfoxide group, a sulfone group, a thiol group, an ortho-ester group, a urea group and an imino group.

[10] A method of oxidizing a carbon-carbon double bond of Compound A as described in any one of the above [1] to [9], wherein Compound A is at least one compound selected from the group consisting of allyl ethers, polyhydric alcohol ethers, carboxylic acid esters and compounds having from 3 to 10 carbon atoms.

[11] A method of oxidizing a carbon-carbon double bond of Compound A as described in the above [10], wherein the allyl ethers are at least one compound selected from the group consisting of an allyl methyl ether, an allyl ethyl ether, an allyl propyl ether, an allyl butyl ether, an allyl vinyl ether and a diallyl ether.

[12] A method of oxidizing a carbon-carbon double bond of Compound A as described in the above [10], wherein Compound A is a diallyl ether or an allyl alcohol and the oxidizing agent is hydrogen peroxide.

[13] A method of oxidizing a carbon-carbon double bond of Compound A as described in the above [10], wherein the polyhydric alcohol ethers are at least one compound selected from the group consisting of an ethylene glycol monoalkenyl ether, an ethylene glycol dialkenyl ether, a 1,2-propanediol monoalkenyl ether, a 1,2-propanediol dialkenyl ether, a 1,3-propanediol monoalkenyl ether, a 1,3-propanediol dialkenyl ether, a 1,2-butanediol monoalkenyl ether, a 1,2-butanediol dialkenyl ether, a 1,3-butanediol monoalkenyl ether, a 1,3-butanediol dialkenyl ether, a 1,4-butanediol monoalkenyl ether, a 1,4-butanediol dialkenyl ether, a trimethylolpropane monoallyl ether, a trimethylolpropane diallyl ether, a trimethylolpropane triallyl ether, a pentaerythritol monoalkenyl ether, a pentaerythritol dialkenyl ether, a pentaerythritol trialkenyl ether and a pentaerythritol tetraalkenyl ether.

[14] A method of oxidizing a carbon-carbon double bond of Compound A as described in the above [10], wherein the carboxylic acid esters are at least one compound selected from the group consisting of an allyl formate, an allyl acetate, an allyl propionate, an allyl tartrate and an allyl methacrylate.

[15] A method of oxidizing a carbon-carbon double bond of Compound A as described in the above [10], wherein the compounds having from 3 to 10 carbon atoms are at least one compound selected from the group consisting of an allyl alcohol, an allyl bromide, an allyl chloride, an acrolein, a methacrolein and an acrylic acid.

[16] A method of oxidizing a carbon-carbon double bond of Compound A as described in any one of the above [1] to [15], wherein the oxidation reaction is performed in the presence of at least one solvent selected from the group consisting of alcohols, ketones, nitriles and water.

[17] A method of oxidizing a carbon-carbon double bond of Compound A as described in any one of the above [1] to [16], wherein the product obtained by the oxidation reaction is a compound resulting from the epoxidation of the carbon-carbon double bond site of the raw material Compound A.

[18] A process for producing an oxidized compound of Compound A, comprising using the oxidation method of a carbon-carbon double bond of Compound A described in any one of the above [1] to [17].

[19] A process for producing an allyl glycidyl ether, a diglycidyl ether or a glycidol, comprising using at least one member selected from the group consisting of a diallyl ether, an allyl alcohol and a mixture thereof, as Compound A and using the oxidation method of a carbon-carbon double bond of Compound A described in any one of the above [1] to [17].

[20] The process for producing an allyl glycidyl ether, a diglycidyl ether or a glycidol as described in the above [19], wherein hydrogen peroxide is used as the oxidizing agent.

Figure 1:
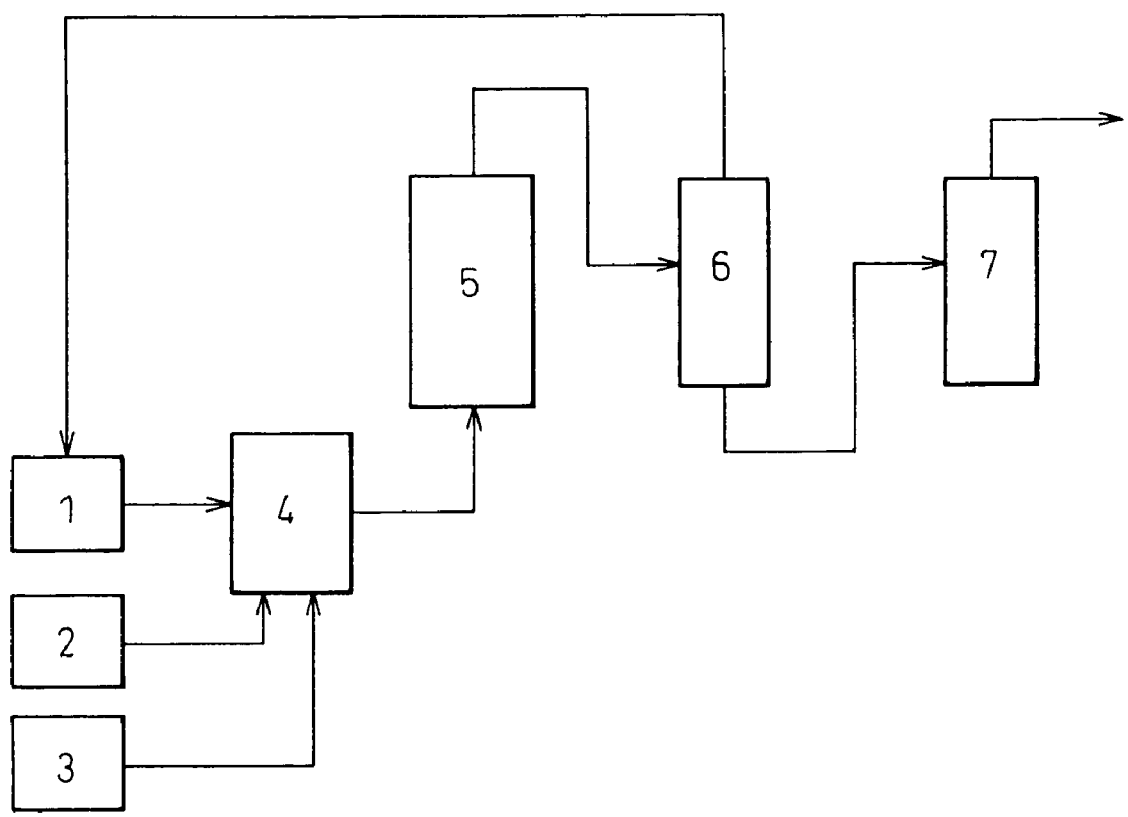
FIG. 1 is a flow chart for specifically illustrating Example 8 and Comparative Example 4.

Respective reference numerals in the figure denote have the following meanings:

1: Tank C; A tank for storing diallyl ether and methanol, as raw materials. Unreacted diallyl ether and methanol are also recovered to the tank C.

2: Tank A; A tank for storing diallyl ether as a raw material.

3: Tank B; A tank for storing aqueous hydrogen peroxide solution of 60 mass %.

4: Mixer; A device for mixing the methanol solution of diallyl ether supplied from the tank C, the diallyl ether supplied from the tank A, and the aqueous hydrogen peroxide solution of 60 mass % supplied from the tank B, so as to prepare a homogeneous solution.

5: Oxidation reactor; A reactor which is filled with titanosilicate catalyst and is to be used to oxidize diallyl ether.

6: Distilling column (or tower) A; A distilling column into which the reaction mixture flowing out of the oxidation reactor is feed. From the column top, unreacted diallyl ether and methanol are collected.

7: Distilling column B; A distilling column for refining the crude allyl glycidyl ether supplied from the bottom of the distilling column A.

BEST MODE FOR CARRYING OUT THE INVENTION

Hereinbelow, the present invention will be described in detail with reference to the accompanying drawings as desired. In the following description, "%" and "part(s)" representing a quantitative proportion or ratio are those based on mass, unless otherwise noted specifically.

The present invention (I) is a method of oxidizing a carbon-carbon double bond of Compound A, comprising the following first to third steps:

First Step:

a step of oxidizing a carbon-carbon double bond of Compound A by using a peroxide as the oxidizing agent in the presence of a titanosilicate catalyst so as to provide a conversion of Compound A in the range of 50 mol % or less to thereby obtain an oxidation reaction mixture;

Second Step:

a step of separating Compound A from the oxidation reaction mixture obtained in the first step; and Third Step:

a step of returning Compound A obtained in the second step to the first step.

At first, the first step is described.

(Titanosilicate Catalyst)

The titanosilicate catalyst to be usable in the first step of the present invention is not limited. Specific examples thereof may include crystalline titanosilicate and porous titanosilicate represented by the following compositional formula (1):

$$x\text{TiO}_2 \cdot (1-x)\text{SiO}_2 \qquad \text{Compositional Formula (1)}$$

(wherein x is from 0.0001 to 0.2).

Herein, "x" in the above formula means the molar ratio of $TiO_2$ present in the titanosilicate and (1−x) is the molar ratio of $SiO_2$ present therein. In other words, x/(1−x) merely shows the molar ratio of titanium/silicon and does not exclude the presence of other elements in the titanosilicate.

In the compositional formula (1), "x" is from 0.0001 to 0.2, preferably from 0.005 to 0.2, more preferably from 0.01 to 0.1. Other than titanium introduced into the skeleton by substituting silicon, titanium species present in the site out of the skeleton (for example, 6-coordination titanium species or anatase-like titanium oxide) may be co-present. However, these titanium species outside the skeleton generally accelerate the side reaction or narrow the pores to inhibit the diffusion of a reactant, and therefore, the amount of these species present may preferably be small.

In the compositional formula (1), the specified x is assumed to be the ratio of titanium contained inside the skeletons. However, in the case where titanium is present outside the skeleton in addition to titanium inside the skeleton, it is actually difficult to precisely determine the titanium contained inside the skeleton. Generally, for example, on the ultraviolet-visible absorption spectrum, the absorption in the vicinity of 210 nm is assigned to titanium inside the skeleton, the absorption in the vicinity of 260 nm is assigned to 6-coordination titanium species outside the skeleton, and the absorption in the vicinity of 330 nm is assigned to anatase-like titanium species. Accordingly, when an absorption is present in the vicinity of 210 nm, it is recognized that the titanosilicate contains titanium inside the skeleton. In fact, the titanosilicate catalyst in the present invention (I) has an absorption in the vicinity of 220 nm and this reveals that titanium is present inside the skeleton. However, when an absorption is present at other wavelengths, in many cases, the ratio of these titanium species present cannot be quantitatively discussed even by combining it with other means such as nuclear magnetic resonance method or infrared absorption method.

The clearly recognizable matter is only that the value in the molar ratio of titanium to silicon calculated from the proportions of titanium and silicon obtained after the composition analysis such as elementary analysis is the maximum value of the amount of titanium contained inside the skeleton. As described above, it is difficult to directly determine the molar ratio of titanium contained inside the skeleton. In the present invention, for convenience, the molar ratio of titanium and silicon calculated as x in compositional formula (1) by the composition analysis is used as the molar ratio of titanium contained inside the skeleton.

(Specific Examples of Titanosilicates)

As described above, specific examples of the crystalline titanosilicate may include crystalline titanosilicates and porous titanosilicates. Specific examples of crystalline titanosilicates may include those having a crystal structure of MFI-type, AEL-type, EUO-type, FER-type, MEL-type, AFI-type, MWW-type, ATO-type, *BEA-type, MOR-type and CLO-type. On the other hand, specific examples of the meso-porous titanosilicate may include meso-porous titanosilicates having a code of FSM-16, MCM-41, MCM-48, MCM-50, SBA-1, SBA-2, SBA-3, HMS, MSU-1, MSU-2, SBA-15 and SBA-16.

Preferred examples of the titanosilicate as a catalyst may include crystalline titanosilicates of MFI-type, MEL-type, MWW-type and EUO-type, and meso-porous titanosilicates MCM-41 and MCN-48. Among these, more preferred are crystalline titanosilicates of MFI-type and MWW-type and meso-porous titanosilicate MCM-41. Of course, these titanosilicates can be used as a mixture of two or more species thereof.

The titanosilicate catalyst for use in the present invention can be prepared by a known method. Specific examples thereof may include MFI-type crystalline titanosilicate (U.S. Pat. No. 4,410,501), *BEA-type crystalline titanosilicate (JP-A-7-242649), MOR-type crystalline titanosilicate (G. J. Kim, B. R. Cho and J. H. Kim, *Catalyst Letters,* 259 (1993)), MCM-41 porous titanosilicate (T. Blasco, *Journal of Catalysis,* 156 (1995)) and MCM-48 porous titanosilicate (Takashi Tatsumi, *Chemical Communication,* 145 (1996)).

The form or shape of the titanosilicate catalyst used in the first step is not particularly limited. In the present invention, it is preferred to use the form thereof (such as a powder, fine spheres, pellets or extrusion-molded articles or supported on a support) which is capable of providing a small pressure loss, when a reactor is packed with such a catalyst. It is also possible to use a binder at the time of the molding of a catalyst. In such a case, it is preferred to use a binder or support (or carrier) which is substantially non-acidic or weakly acidic substance which does not accelerate the decomposition reaction of the peroxide or the decomposition reaction of the intended oxidized compound.

(Oxidizing Reaction)

In the oxidizing reaction at the first step of the present invention, only the oxidizing reaction of the carbon-carbon double bond of Compound A can be selectively performed without affecting other functional group excluding the carbon-carbon double bond. Of course, the other functional group excluding the carbon-carbon double bond can be reacted to obtain an utterly different intended product, and such a case is also included in the present invention.

According to the present inventor's investigation and knowledge, the reason for providing the above-mentioned excellent selectivity in the present invention may presumably be that the titanosilicate to be used in the present invention generally has a high oxidizing activity on a carbon-carbon double bond, but has a low oxidizing activity on another functional group (on the contrary, "TS-1" exceptionally has a tendency to also oxidize another functional group).

(Peroxides)

The peroxide usable in the first step of the present invention is not particularly limited. Specifically examples thereof may include hydrogen peroxide and organic peroxides. Examples of the organic peroxide may include: tert-butyl hydroperoxide, tert-amyl hydroperoxide, cumene hydroperoxide, ethylbenzene hydroperoxide, cyclohexyl hydroperoxide, methylcyclohexyl hydroperoxide, isobutylbenzene hydroperoxide, ethylnaphthalene hydroperoxide and peracetic acid. However, the peroxides usable in the present invention are not limited to these specific examples. These peroxides may be used in combination of two or more thereof.

In view of easy availability and treatment after the reaction, the peroxide may most preferably be hydrogen peroxide. The hydrogen peroxide can be used in any concentration. For example, an aqueous hydrogen peroxide solution having a concentration of 30 mass %, 60 mass % or 90 mass %, which is commercially available in industry, can be used.

(Compound A)

The "Compound A" used in the first step of the present invention is not particularly limited. Any compound can be used as long as it is a compound having at least two or more functional groups within one molecule thereof and at least one of these functional groups is a carbon-carbon double bond. In this case, the other functional group of Compound A excluding the carbon-carbon double bond essential to the Compound A may contain a carbon-carbon double bond, or the other functional group may also be another carbon-carbon double bond.

Specific examples of the other functional group may include: an alkenyl group, an alkynyl group, an aryl group, an alcohol group, a phenol group, an ether group, an epoxide group, a halogen atom, a carbonyl group, an amide group, a cyanate group, an isocyanate group, a thiocyanate group, an amino group, a diazo group, a nitro group, a nitrile group, a nitroso group, a sulfide group, a sulfoxide group, a sulfone group, a thiol group, an orthoester group, a urea group and an imino group. However, the present invention is not limited to these specific examples. The compound may have two or more same functional groups or may have two or more kinds of functional groups.

In the present invention, specific examples of the "other functional group" may include alkenyl group, aryl group, alcohol group, and phenol group.

(Specific Examples of Compound A)

More specific examples of Compound A may include allyl ethers, ethers of polyhydric alcohol, carboxylic acid esters and other compounds having 3 to 10 carbon atoms. Of course, a mixture of two or more thereof may be used.

More specifically, examples of the allyl ethers may include allyl methyl ether, allyl ethyl ether, allyl propyl ether, allyl butyl ether, allyl vinyl ether and diallyl ether.

Examples of the ethers of polyhydric alcohol may include ethylene glycol monoalkenyl ether, ethylene glycol dialkenyl ether, 1,2-propanediol monoalkenyl ether, 1,2-propanediol dialkenyl ether, 1,3-propanediol monoalkenyl ether, 1,3-propanediol dialkenyl ether, 1,2-butanediol monoalkenyl ether, 1,2-butanediol dialkenyl ether, 1,3-butanediol monoalkenyl ether, 1,3-butanediol dialkenyl ether, 1,4-butanediol monoalkenyl ether, 1,4-butanediol dialkenyl ether, trimethylolpropane monoallyl ether, trimethylolpropane diallyl ether, trimethylolpropane triallyl ether, pentaerythritol monoalkenyl ether, pentaerythritol dialkenyl ether, pentaerythritol trialkenyl ether and pentaerythritol tetraalkenyl ether.

Examples of the carboxylic acid esters may include allyl formate, allyl acetate, allyl propionate, allyl tartrate and allyl methacrylate.

Examples of the compounds having from 3 to 10 carbon atoms may include allyl alcohol, allyl bromide, allyl chloride, acrolein, methacrolein and acrylic acid.

(Preferred Compound A)

In view of a large number of industrial applications of the oxidized product of Compound A, Compound A may preferably be allyl chloride, diallyl ether, allyl acetate, allyl methacrylate or allyl alcohol. Compound A may most preferably be diallyl ether, allyl alcohol or a mixture thereof. As described above, the oxidizing agent may preferably be hydrogen peroxide and the combination of this with diallyl ether, allyl alcohol or a mixture thereof is a most preferred example of the combination of an oxidizing agent and Compound A in the oxidizing method.

In this case, when diallyl ether is used as Compound A, allyl glycidyl ether, diglycidyl ether or a mixture thereof can be obtained as the oxidized compound. When allyl alcohol is used as Compound A, glycidol can be obtained as the oxidized compound.

The conversion of Compound A in the first step is 50 mol % or less, preferably 30 mol % or less, more preferably 15 mol % or less. The "conversion of Compound A" as used herein means a ratio of Compound A consumed by the reaction to Compound A which has been present before the reaction. If the conversion of Compound A exceeds 50 mol %, the selectivity of Compound A to the oxidized compound may be worsened and this is not preferred.

(Regeneration of Catalyst)

The titanosilicate catalyst used in the oxidizing method of a carbon-carbon double bond of Compound A by using a peroxide as the oxidizing agent fails to exhibit the initial activity, with the lapse of time or after repeated use thereof, because a coke material or the like adheres to the inside of pores. This activity deterioration due to adhesion of coke material is considered to be a reversible deterioration, and in many papers, it is reported that the deteriorated catalyst can be regenerated to the initial activity by an aeration treatment. Examples thereof may include a regeneration method of a titanium-containing molecular sieve catalyst, comprising heating the catalyst at a temperature of 150 to 400° C. (see, JP-A-8-309200).

However, the titanosilicate catalyst deteriorated in the activity after performing the oxidizing reaction in the first step of the present invention so as to provide a conversion of Compound A of 50 mol % or more does not exhibit the initial activity, even when a conventionally known regeneration treatment by aeration is performed. According to the present inventors' investigation and knowledge, it is presumed that when the oxidizing reaction is performed so as to provide a conversion of Compound A of 50 mol % or more, the deterioration in the activity of the catalyst is caused not only by the clogging of pores due to adhesion of coke but also by the decrease of the titanium concentration in the catalyst resulting from the flowing out of titanium atoms as the active site of the catalyst during the reaction. That is, if the oxidizing reaction is performed so as to provide a conversion of Compound A of 50 mol % or more, the titanosilicate catalyst undergoes permanent deterioration of not showing the initial activity even when regenerated by aeration. Accordingly, the conversion of Compound A in the first step may preferably be 50 mol % or less, more preferably 30 mol % or less, still more preferably 15 mol % or less.

(Method of Controlling Conversion)

The method of controlling the conversion of Compound A is not particularly limited. For example, the conversion can be controlled by the amount of titanosilicate catalyst used in the reaction, the reaction temperature or the peroxide concentration in the raw material composition. A reaction method using the peroxide as a limited reaction component is preferred. The "limited reaction component" as used herein means a raw material component supplied at a smallest ratio when a ratio of the material amount (mol) of each raw material component in the raw material supplied is determined on the basis of a certain component (standard) among the respective raw material components to be supplied to the reactor, and this ratio is compared with the ratio required from the stoichiometric formula with respect to the details of the "limited reaction component", Kenji Hashimoto, "*Hanno Kogaku (Reaction Engineering)*", pp. 39, revised edition, Baifukan (Sep. 30, 1993) may be referred to). When the peroxide is a limited reaction component, the maximum value achievable for the conversion of Compound A can be easily controlled by the material amount of peroxide.

The concentration of the peroxide as a limited reaction component in the raw material is not particularly limited but may preferably be 30 mass % or less, more preferably 15 mass % or less, still more preferably 10 mass % or less, based on the mass of total components to be supplied to the reactor. If the peroxide concentration exceeds 30 mass %, a self decomposition reaction of the peroxide vigorously occurs and a danger of explosion disadvantageously arises due to the generation of oxygen.

In the present invention, the conversion of the oxidizing agent is not particularly limited but is based on the increment or decrement of the oxidizing agent itself between before and after the reaction and the amount before the reaction, the conversion may preferably be 50 mol % or more, more preferably 75 mol % or more, still more preferably 90 mol % or more.

If the conversion of the oxidizing agent is less than 50 mol %, unreacted peroxide remains during the reaction to cause a self decomposition reaction of the peroxide and disadvantageously, the peroxide must be separated and recovered from the mixture after the completion of reaction. Further, in the case where the peroxide is difficult to separate, the peroxide must be decomposed in view of safety and the selectivity of the peroxide is worsened. Therefore, the conversion of the oxidizing agent may preferably be 50 mol % or more.

(Amount of Titanosilicate)

The amount of the titanosilicate catalyst used for the oxidizing reaction in the first step is not particularly limited. The preferred range thereof varies depending on the activity of titanosilicate catalyst, the kind of oxidizing reaction, the reactivity of substrate, the peroxide concentration and the reaction form (batch system or continuous system). In the case of use in a slurry system, usually, the amount of the titanosilicate catalyst is, in terms of the concentration in the reactant mixture, suitably from 0.1 to 20 mass %, preferably from 0.5 to 10 mass %. In a fixed bed flow reaction system, the titanosilicate catalyst may preferably be used in an apparent catalytic amount larger than this range.

(Solvent)

The oxidizing reaction in the first step of the present invention (I) may be performed without using a solvent or in the presence of an appropriate solvent.

Examples of the appropriate solvent may include alcohols, ketones, nitrites and water. Specific examples of the alcohols may include methanol, ethanol, 1-propanol, 2-propanol, 1-butanol, 2-butanol, tert-butanol, amyl alcohol, ethylene glycol, propylene glycol and 1,2-butanediol. Specific examples of the ketones may include acetone, methyl ethyl ketone and diethyl ketone. Specific examples of the nitrites may include acetonitrile, propionitrile and benzonitrile. These solvents may be used individually or as a mixture. Among these solvents, in view of the compatibility of the solvent with the Compound A and the oxidizing agent, and in view of the stability of the oxidizing agent in the solvent, preferred are acetone, methanol, acetonitrile and water, and more preferred are methanol and water.

It is preferred to use the solvent in an amount of 0.5 to 100 times that of the mass of Compound A, while the amount of the solvent can be changed depending on the kind of the oxidizing agent, Compound A, and combinations thereof.

(Reaction Temperature of Oxidizing Reaction)

The reaction temperature at the oxidizing reaction in the first step of the present invention (I) is not particularly limited and may preferably be from 0 to 150° C., more preferably from 10 to 100° C. If the reaction temperature is less than 0° C., the reaction rate is low and not practical, whereas if it exceeds 150° C., the decomposition reaction of the peroxide seriously occurs and also, the decomposition reaction of the intended product may be disadvantageously accelerated.

The oxidizing reaction is generally an exothermic reaction and therefore, the heat of reaction may preferably be removed by an appropriate method so as to control the reaction temperature in a constant range. The reaction pressure is not particularly limited.

The oxidizing reaction in the first step of the present invention may be performed by a batch system, a continuous system or a semi-continuous system using an appropriate reactor such as fixed bed reactor, moving layer reactor, fluidized bed reactor, vessel-type reactor or continuous stirring vessel-type reactor and any method may be used. The mixture comprising a titanosilicate catalyst, Compound A and a peroxide may be mixed in any manner and the components may be mixed all at once or in sequence.

As described above, in the first step of the present invention (I), the oxidizing reaction of the carbon-carbon double bond of Compound A is performed using a peroxide as the oxidizing agent in the presence of a titanosilicate catalyst while suppressing the conversion of Compound A, whereby the intended oxidized compound can be obtained with high selectivity. In a general oxidizing method, when the conversion of the raw material compound is low and a sufficiently high concentration of the intended oxidized compound in the reaction mixture cannot be obtained, this production process incurs worsening of the productivity and is not suitable as an industrial method in many cases.

However, the present invention (I) comprises the following second and third steps subsequently to the first step, so that in the oxidizing method of a carbon-carbon double bond of Compound A, an intended oxidizing reaction can be performed at a high productivity without impairing the selectivity of the oxidizing reaction.

The second and third steps are described below.

(Second Step)

In the present invention (I), the second step is a step of separating Compound A from the reaction mixture obtained in the first step.

The method of separating Compound A from the reaction mixture in the second step of the present invention is not particularly limited. In the case where the reactor used for the oxidizing reaction in the first step is a stirring vessel-type reactor, Compound A may be separated from the reaction mixture Using an arbitrary method after recovering the titanosilicate catalyst by appropriate means such as filtration or centrifugation or Compound A may be separated from the reaction mixture containing the titanosilicate catalyst without recovering the catalyst.

On the other hand, in the case where the reactor used for the oxidizing reaction in the first step is a fixed bed-type reactor, a reaction mixture containing no titanosilicate catalyst can be easily obtained from the outlet of the reactor while holding the titanosilicate catalyst in the reactor and Compound A can be separated from the obtained reaction mixture containing no titanosilicate catalyst by an arbitrary method.

(Preferred Separation Method)

The preferred method of separating Compound A from the reaction mixture of the first step varies depending on Compound A, the boiling point of the oxidized product, the kind of the functional group and the heat stability. For example, when Compound A has a standard boiling point of 30 to 150° C. under an atmospheric pressure, the separation from the reaction mixture of the first step may preferably be performed by a fractional distillation method at an operation temperature of 30 to 200° C. under an atmospheric pressure. Examples of Compound A having a boiling point of 30 to 150° C. under an atmospheric pressure may include allyl methyl ether, allyl ethyl ether, allyl propyl ether, allyl butyl ether, allyl vinyl ether, diallyl ether, allyl bromide, allyl chloride, methacrolein, allyl formate, allyl acetate, allyl propionate, allyl tartrate and allyl methacrylate.

In the case where Compound A is a compound having high solubility in water, such as allyl alcohol, acrolein, acrylic acid and ethylene glycol monoalkenyl ether, separation by liquid-liquid extraction using an organic solvent as an extracting agent is preferred and the operation temperature therefor may preferably be from 15 to 200° C. If the operation temperature exceeds this range, the oxidized compound as the product may decompose and this is not preferred.

Further, when Compound A has a boiling point of 150° C. or more under an atmospheric pressure, separation from the reaction mixture may preferably be performed by distillation under reduced pressure or by liquid-liquid separation using an organic solvent as the extracting agent. The pressure in the distillation under reduced pressure may preferably be from 133 Pa to 100 kPa and the operation temperature may preferably be from 20 to 200° C. The organic solvent used for the liquid-liquid extraction may preferably be an acetic acid ester compound, an ether compound, an aromatic compound or an aliphatic saturated hydrocarbon compound and the operation temperature is from 20 to 150° C.

Examples of Compound A having a boiling point of 150° C. or more under an atmospheric pressure may include ethers of polyhydric alcohol, such as ethylene glycol dialkenyl ether, 1,2-propanediol monoalkenyl ether, 1,2-propanediol dialkenyl ether, 1,3-propanediol monoalkenyl ether, 1,3-propanediol dialkenyl ether, 1,2-butanediol monoalkenyl ether, 1,2-butanediol dialkenyl ether, 1,3-butanediol monoalkenyl ether, 1,3-butanediol dialkenyl ether, 1,4-butanediol monoalkenyl ether, 1,4-butanediol dialkenyl ether, trimethylolpropane monoallyl ether, trimethylolpropane diallyl ether, trimethylolpropane triallyl ether, pentaerythritol monoalkenyl ether, pentaerythritol dialkenyl ether, pentaerythritol trialkenyl ether and pentaerythritol tetraalkenyl ether.

(By-product Having Hydroxyl Group)

In the case where a by-product having a hydroxyl group produced from the peroxide has a possibility of causing a reaction with Compound A or an oxidized compound thereof at an arbitrary operation for separating Compound A from the reaction mixture, the by-product having a hydroxyl group produced from the peroxide may preferably be removed in advance of the arbitrary operation for separating Compound A from the reaction mixture. Examples of the by-product having a hydroxyl group produced from the peroxide may include water, tert-butyl alcohol, tert-amyl alcohol, 2-phenyl-2-propanol, 1-phenyl ethanol, cyclohexenol, methylcyclohexenol, 2-methyl-2-hydroxyl-3-phenyl-propane and acetic acid. The method of removing the by-product having a hydroxyl group produced from the peroxide is not particularly limited but examples of the removing method may include distillation, liquid-liquid extraction, liquid-liquid separation and membrane separation.

In the case where the by-product having a hydroxyl group produced from the peroxide is water, as water has high nucleophilicity and a decomposition reaction of the oxidized product readily occurs, water may preferably be removed from the reaction mixture before the arbitrary operation for separating Compound A from the reaction mixture. The method of removing water is not particularly limited but examples thereof may include liquid-liquid separation, liquid-liquid extraction, distillation and membrane separation (with respect to the details of the removing methods, Tarama laboratory of Kyoto University, "Hanno-betsu Shokubai Bunrui-Hyo 2 (Table 2 of Classification of Catalysts Corresponding to Reactions)", pp. 221–232, published May 1, 1972, Kagaku Kogyo Sha may be referred to).

(Removal of Water)

When the by-product having a hydroxyl group to be produced from the oxidizing agent is water, the nucleophilicity of water is high, and the oxidizing agent is liable to cause a degradation reaction. Therefore, in such a case, it is preferred to remove water from the reaction mixture, before any operation for separating the Compound A from the reaction mixture. The method of removing water is not particularly limited, but specific examples of the removing method may include liquid-liquid separation, liquid-liquid extraction, distillation, membrane separation, etc.

In the removal of water using liquid-liquid separation, the reaction mixture may be subjected as it is to the liquid-liquid separation without adding any material, however, the liquid-liquid separation may preferably be performed after adding an inorganic salt to the reaction mixture and thereby decreasing the concentration of the oxidized compound in the aqueous phase. Examples of the inorganic salt added may include lithium acetate, sodium acetate, magnesium acetate, aluminum acetate, potassium acetate, lithium chloride, sodium chloride, magnesium chloride, aluminum chloride, potassium chloride, lithium sulfate, sodium sulfate, magnesium sulfate, aluminum sulfate and potassium sulfate.

The extracting agent usable in the method of removing water using liquid-liquid extraction is not particularly limited. However, in view of the separation factor and selectivity at the time of the extraction of water and the oxidized product, the extracting agent may preferably be a carboxylic acid ester and specific examples thereof may include methyl formate, ethyl formate, propyl formate, butyl formate, allyl formate, methyl acetate, ethyl acetate, propyl acetate, butyl acetate, allyl acetate, methyl propionate, ethyl propionate, propyl propionate, butyl propionate and allyl propionate.

In the method of removing water by distillation, the distillation method is not particularly limited but since much energy is usually necessary for the distillation of water, the distillation method may preferably be, for example, an azeotropic distillation method. The preferred compound having an azeotropic composition with water for use in the azeotropic distillation may be previously present in the reaction mixture or may be newly added as an azeotropic agent to the reaction mixture. Also, an azeotropic agent may be further added to the reaction mixture where the compound having an azeotropic composition with water is previously present. In selecting the azeotropic agent, an azeotropic agent having an azeotropic temperature with water of 200° C. or less under an atmospheric pressure is preferred and a compound not exhibiting acidity is preferred so as to prevent decomposition of the oxidized compound.

(Unreacted Peroxide)

In the separation of Compound A from the reaction mixture, an unreacted peroxide may be present in the reaction mixture but in order to avoid a danger of explosion due to concentration of the unreacted peroxide, the unreacted peroxide may preferably be removed before separating Compound A from the reaction mixture. The method of removing the unreacted peroxide is not particularly limited, and the peroxide may be separated as it is from the reaction mixture or may be decomposed and thereby removed from the reaction mixture. The separation of the peroxide from the reaction mixture and the decomposition of the peroxide can be performed by a conventionally known method.

Examples of the method of separating the peroxide from the reaction mixture may include distillation, liquid-liquid separation and liquid-liquid extraction. Examples of the method of decomposing the peroxide may include a method of adding an inorganic salt to the reaction mixture and a method of contacting the reaction mixture with a metal catalyst.

In the method of separating the peroxide, when the peroxide is hydrogen peroxide or peracetic acid readily soluble in water, liquid-liquid extraction using water as the extracting agent is preferred. In the case where the peroxide is difficulty soluble in water such as tert-butyl hydroperoxide, cumene hydroperoxide and ethylbenzene hydroperoxide, distillation is preferred. The temperature at the liquid-liquid extraction may preferably be from 20 to 200° C. and the pressure is not particularly limited. Of course, the peroxide recovered can be again returned to the first step and reused.

In the method of adding a reducing material to the reaction mixture and thereby decomposing the peroxide, the inorganic salt added is not particularly limited, but examples thereof may include sodium thiosulfate, cerium sulfate and potassium permanganate. The amount of the inorganic salt added is not particularly limited, and may be either grater or smaller than the molar amount of the remaining peroxide, however, the amount added may preferably be from 30 to 200 mol %, more preferably from 50 to 120 mol %, based on the molar amount of the remaining peroxide. The inorganic salt added may be in any form and may be added in the form of a solid as it is or in the form of an aqueous solution. At the time of adding the inorganic salt, the temperature of the reaction mixture is not particularly limited but since the decomposition reaction of the peroxide is an exothermic reaction, the temperature may preferably be from 20 to 180° C., more preferably from 30 to 150° C.

(Metal Catalyst)

The metal catalyst used in the method of contacting the reaction mixture with a metal catalyst and thereby decomposing the peroxide is not particularly limited but the metal catalyst may preferably be at least one metal selected from the group of iron, copper, nickel, manganese, platinum and palladium, a chloride, an oxide or a sulfide thereof. This metal may be added in any form and may be used in the form of a particle as it is or may be used after dissolving it in a solution or loading it on a support (with respect to the details of the metal catalysts, Tarama laboratory of Kyoto University, "Hanno-betsu Shokubai Bunrui-Hyo 2 (Table 2 of Classification of Catalysts Corresponding to Reactions)", pp. 221–232, published May 1, 1972, Kagaku Kogyo Sha may be referred to).

(Third Step)

The third step of the present invention (I) is a step of returning Compound A obtained in the second step to the first step.

Compound A obtained in the second step may be returned as it is to the first step or may be purified by any method and then returned to the first step. The purity of Compound A returned to the first step is not particularly limited but when a component acting as a catalyst poison of the titanosilicate catalyst in the first step is contained, Compound A obtained in the second step may preferably be purified.

(Catalyst Poison)

The component acting as a catalyst poison of the titanosilicate catalyst in the first step is not particularly limited. However, in view of the coordinating force thereof and the affinity thereof with titanium, the component acting as a catalyst poison may include an epoxide open-ring product as a by-product produced in the method of producing an epoxide compound from Compound A, an alcohol compound and an aldehyde compound.

Specific examples of the epoxide open-ring product may include a diol compound produced from epichlorohydrin, a diol compound produced from glycidol, a diol compound produced from glycidyl methacrylate, a diol compound produced from glycidyl acetate, and a diol compound produced from allyl glycidyl ether. Specific examples of the alcohol compound may include methanol, ethanol, propanol, vinyl alcohol, allyl alcohol, ethylene glycol, 1,2-propanediol, 1,3-propanediol, 1,4-butanediol, trimethylolpropane and pentaerythritol. Specific examples of the aldehyde compound may include formaldehyde, acetaldehyde, propionaldehyde, butylaldehyde and acrolein.

The catalytic poison components which are particularly preferably removed are a diol compound produced from epichlorohydrin, a diol compound produced from glycidol, a diol compound produced from allyl glycidyl ether, vinyl alcohol, allyl alcohol, 1,3 -propanediol, 1,4-butanediol, trimethylolpropane, formaldehyde, acetaldehyde, propionaldehyde and acrolein.

Examples of the method of removing the component acting as a catalyst poison of the titanosilicate catalyst in the first step may include liquid-liquid separation, liquid-liquid extraction, distillation and membrane separation, however, the present invention is not particularly limited, thereto. The form of Compound A returned from the second step to the first step is not particularly limited and may be any of a gas state, a liquid state and a solid state. The temperature and the pressure are not limited.

(Recycling)

Compound A obtained in the second step only can be returned to the first step but so-called "recycling" of the chemical process may preferably be established by returning it after newly adding Compound A thereto. In general, a method of adding new Compound A in an amount corresponding to the amount of Compound A converted into the oxidized compound in the oxidizing reaction or in an amount at least larger than that and then returning these to the first step is more preferred.

If new Compound A is not added, the concentration of Compound A in the first step decreases and a sufficiently high reaction rate is disadvantageously difficult to obtain. On the other hand, when new Compound A is added in an amount at least larger than the amount of Compound A converted into the oxidized compound and these are returned to the first step, Compound A in the first step can be kept at a constant concentration or more and the oxidizing reaction can be stable performed.

(Process for Producing Oxidized Compound)

The present invention (II) is described below. The present invention (II) is a process for producing an oxidized compound of Compound A, comprising using the oxidizing method of the present invention (I).

As long as the first to third step described in the oxidizing method of the present invention (I) are contained, the process for producing an oxidized compound of Compound A of the present invention (II) may comprise any other steps. A step of decomposing/removing the peroxide used as the oxidizing agent as exemplified in the present invention (I) or a step of purifying Compound A obtained in the third step may be provided.

Compound A as a raw material, the oxidizing agent, the titanosilicate catalyst, the temperature and pressure in the oxidizing reaction, the reaction conditions such as compositional ratio, and the like which can be applied to the production process of the present invention (II) all are the same as those used in the oxidizing method of the present invention (I). The product is also the same as in the present invention (I).

EXAMPLES

The present invention is described in greater detail below by referring to Examples, however, these Examples only show the outline of the present invention and the present invention is not particularly limited, to these Examples.

Description of Terms in Examples and Comparative Examples

Method of Calculating Conversion of Diallyl Ether:

The conversion of diallyl ether is shown by a molar ratio of diallyl ether consumed in the reaction to the diallyl ether charged before the reaction. The diallyl ether consumed in the reaction was calculated from the increase or decrease of diallyl ether between before and after the reaction.

Method of Calculating Selectivity of Allyl Glycidyl Ether:

The selectivity of allyl glycidyl ether is shown by a molar ratio of the amount of the allyl glycidyl ether produced, which was calculated from the analysis results of the filtrate after the reaction, to the diallyl ether consumed in the reaction.

Method of Calculating Conversion of Hydrogen Peroxide:

The conversion of hydrogen peroxide is shown by a ratio of hydrogen peroxide consumed in the reaction to the hydrogen peroxide charged before reaction. The hydrogen peroxide consumed in the reaction was calculated from the increase or decrease of hydrogen peroxide between before and after the reaction.

The yield is an yield of epoxide compound as an intended oxidized compound, based on hydrogen peroxide, after the completion of oxidizing reaction using hydrogen peroxide and shown by a molar ratio of the amount of the epoxy compound produced to the hydrogen peroxide charged.

Calculation of Efficiency of Hydrogen Peroxide:

The efficiency of hydrogen peroxide is shown by a ratio of hydrogen peroxide consumed in the reaction excluding the hydrogen peroxide consumed in the decomposition into oxygen, namely, a ratio of hydrogen peroxide consumed in the epoxidizing reaction out of the hydrogen peroxide consumed.

Analyzers in Examples and Comparative Examples

Method of Analyzing Titanosilicate Element

About 100 mg of a sample of titanosilicate, which had been dried at 90° C. for 6 hours, was accurately weighed in a Teflon (polytetrafluoroethylene; PTFE) beaker, and about 10 ml of hydrofluoric acid (concentration: 50% by mass) was added to the beaker containing the titanosilicate therein. Then, the Teflon beaker to which the hydrofluoric acid had been added was placed on a hot-plate, and was heated at 150° C. for 3 hours. After the heating for 3 hours, after the disappearance of the liquid component was confirmed, about 10 ml of a 1:1 hydrochloric acid solution (a mixture obtained by mixing 35%-hydrochloric acid and distilled water at a 1:1 ratio) was added to the beaker. Then, the beaker was placed on a hot-plate, and was heated at 150° C. for 3 hours. The thus obtained hydrochloric acid solution was placed in a 100 ml-measuring flask, and the total volume of the solution was adjusted to 100 ml. The resultant solution was used as a sample for ICP measurement.

The thus obtained solution was subjected to a component analysis for titanium, silicon and boron by using a desktop-type plasma emission analysis apparatus (SPS 1700, mfd. by Seiko Denshi Kogyo K.K.). In this analysis, the titanium concentration was measured by using a wavelength of 334.9410 nm, the silicon concentration was measured by using a wavelength of 251.611 nm, and the boron concentration was measured by using a wavelength of 249.7730 nm.

Analysis of Organic Compound Concentration in Filtrate of Reaction Mixture:

The concentration was measured by the following gas chromatography analyzer under the following conditions.

The analysis was performed according to an internal standard method by injecting a 0.4 µl portion of the analysis solution which was obtained by adding 1 ml of 1,4-dioxane as the internal standard to 10 ml of the reaction solution.

Gas Chromatography:

GC-14B manufactured by Shimadzu Corporation

Column:

capillary column TC-WAX (length: 30 m, inner diameter: 0.25 mm, membrane thickness: 0.25 µm)

Carrier Gas:

nitrogen (split ratio: 20, column flow rate: 2 ml/min)

Temperature Conditions:

The detector and the vaporization chamber were at a temperature of 200° C., and the column temperature was kept at 50° C. for 5 minutes from the start of analysis, then elevated to 150° C. at a temperature rising rate of 10° C./min, kept at 150° C. for 10 minutes, thereafter elevated to 200° C. at a temperature rising rate of 10° C./min, and kept for 25 minutes.

Detector:

FID ($H_2$ pressure: 70 kPa, air pressure: 100 kPa)

Analysis of Concentration of Hydrogen Peroxide in Filtrate of Reaction Mixture:

A potentiometric titration was performed by using an automatic potentiometric titrating apparatus AT-012 mfd. by Kyoto Denshi Kagaku Kogyosha and by using an aqueous solution containing Ce(IV) as a titration reagent, to thereby measure the hydrogen peroxide concentration in the filtrate of a reaction mixture. More specifically, 40 ml of ion-exchanged water was added to a 100 ml-glass beaker, and then about 0.3 g of a sample of the filtrate of the reaction mixture to be measured was accurately weighed out in the beaker. Thereafter, potentiometric titration was performed by means of the above automatic potentiometric titrating apparatus by slowly adding to the beaker a 0.1 mol/1-aqueous solution which had been prepared by using tetraammonium cerium sulfate dihydrate (produced by Wako Pure Chemical Industries, Ltd.). The hydrogen peroxide concentration was calculated from the amount of the above 0.1 mol/1-aqueous tetraammonium cerium sulfate solution which had been required for the potentiometric titration until the end point thereof, and the weight of the filtrate of the reaction mixture which had been used for the analysis.

Reference Example

Preparation Method of MFI-Type Crystalline Titanosilicate Catalyst

In a 500 ml-volume beaker equipped with a magnetic stirrer, 62.5 g of tetraethyl orthosilicate (produced by Wako Pure Chemical Industries, Ltd.) was added and then 107 g of an aqueous 20 mass % tetrapropylammonium hydroxide solution (produced by Tokyo Kasei Kogyo) was added at a temperature of 30° C. over 10 minutes.

After stirring for 1.0 hour, a mixture containing 38 g of isopropyl alcohol (produced by Wako Pure Chemical Industries, Ltd.) and 14 g of tetra-orhtotitanate (produced by Tokyo Kasei) was added over 30 minutes. After stirring at 30° C. for 30 minutes, the mixture was heated using a hot bath at 80° C. and the stirring was continued for 2 hours. To the thus-obtained mixture, 230 g of water was added. The resulting solution was transferred to a Teflon-made autoclave (i.e., an autoclave having a Teflon-made cylinder in the inside thereof) and a hydrothermal synthesis was performed at 175° C. for 48 hours. After the completion of hydrothermal synthesis, the contents were taken out from the autoclave and the solid product was separated by centrifugation. The obtained solid product was washed with distilled water and after the completion of washing, calcined at 500° C. for 8 hours in the presence of air to remove organic materials. The solid matter obtained by the calcination was subjected to acid washing for 12 hours using 20 ml of an aqueous 1.0 mol/liter nitric acid solution per 1 g of the solid matter. After the completion of acid washing, the solid product was separated by filtration and then calcined at 500° C. for 12 hours in the presence of air to obtain intended MFI-Type Titanosilicate Catalyst 1 having a titanium/silicon molar ratio of 0.0222.

Example 1

Production of Oxidized Compound Using Crystalline MFI-Type Titanosilicate Catalyst 1

In a 20 ml-volume three-neck flask equipped with a thermometer, a reflux condenser and a magnetic stirrer, 8.0 g (81.5 mmol) of diallyl ether was added and then MFI-Type Titanosilicate Catalyst 1 (100 mg) prepared in Reference Example was charged. The mixture was heated in a hot bath at 60° C. and vigorously stirred. Immediately after the temperature of the reaction mixture reached 57° C., 2.0 g (35.3 mmol as hydrogen peroxide) of an aqueous 60 wt % hydrogen peroxide solution was added to the system. By setting the reaction start time to this point, the stirring was continued until the passing of 60 minutes from the start of reaction.

After 60 minutes from the start of reaction, the reaction mixture was immediately cooled with ice to stop the reaction. Thereafter, the reaction mixture was filtered to separate the liquid component (unreacted diallyl ether, unreacted hydrogen peroxide, water, product and solvent) from the solid component (catalyst). This separation was conducted by placing the reaction mixture in a 50 ml-syringe (Terumo Syringe, mfd. by Terumo K.K.) equipped with a filter (Shodex DTMX-25K), and applying a pressure to the reaction mixture so as to effect filtration.

At this time, the concentration of organic material in the obtained filtrate was analyzed by gas chromatography and the concentration of unreacted hydrogen peroxide was determined by potentiometric titration using Ce(IV). The reaction results are shown in Table 1.

As shown in the reaction results in Table 1, the conversion of diallyl ether was 4.42% and the selectivity of allyl glycidyl ether as the produced epoxy compound was 83.9%.

TABLE 1

|  | Conversion of Diallyl Ether[*1] (%) | Selectivity of Allyl Glycidyl Ether[*2] (%) |
|---|---|---|
| Example 1 | 4.42 | 83.9 |
| Example 2 | 9.07 | 82.7 |
| Example 3 | 13.2 | 81.7 |
| Example 4 | 15.8 | 79.2 |

[*1]Conversion of diallyl ether: Diallyl ether consumed (mol)/raw material diallyl ether (mol) × 100 (%)
[*2]Selectivity of allyl glycidyl ether: Allyl glycidyl ether (mol)/{diallyl ether consumed (mol)} × 100 (mol %)

Example 2

Production of Oxidized Compound Using Crystalline MFI-Type Titanosilicate Catalyst 1

The same operation as in Example 1 was performed except for using 300 mg of MFI-Type Titanosilicate 1. The reaction results are shown in Table 1.

Example 3

Production of Oxidized Compound Using Crystalline MFI-Type Titanosilicate Catalyst 1

The same operation as in Example 1 was performed except for using 500 Mg of MFI-Type Titanosilicate 1. The reaction results are shown in Table 1.

Example 2

Production of Oxidized Compound Using Crystalline MFI-Type Titanosilicate Catalyst 1

The same operation as in Example 1 was performed except for using 800 mg of MFI-Type Titanosilicate 1. The reaction results are shown in Table 1.

Example 5

Continuous Use Test Using Crystalline MFI-Type Titanosilicate

An MFI-type titanosilicate catalyst (molar ratio of titanium and silicon: 0.0233) prepared in the same manner as in Reference Example was molded into a cylindrical pellet having a diameter of 3.0 mm and a height of 7.0 mm and 15.0 g of the pellet was filled in a glass-made reactor (diameter: 35 mm, height: 300 mm). The outside of the reaction tube was heated at 60° C. and from the bottom of the reaction tube, 25.0 g of a mixture of diallyl ether (concentration: 40.0 wt %), hydrogen peroxide (2.84 wt %), water (6.63 wt %) and methanol (50.53 wt %) was fed using a pump.

The reaction solution outflowed for 1.0 hour from the start of reaction was collected, the organic material concentration was analyzed using gas chromatography and also the concentration of unreacted hydrogen peroxide was determined by potentiometric titration using Ce(IV). This operation was repeated until the passing of 50 hours and the reaction results during this time were recorded.

After the passing of 50 hours, the catalyst was taken out from the reaction tube and regenerated by performing a heating treatment at 300° C. for 3 hours in an air atmosphere. After the completion of regeneration treatment, the catalyst was cooled to 30° C. and again filled in the reaction tube and in the same manner as in the 1st time reaction, the reaction of the 2nd time was performed until the passing of 50 hours while recording the reaction results every one hour. Similarly to the first time reaction, this catalyst was taken out and regenerated by performing a heating treatment at 300° C. for 3 hours in an air atmosphere. The 3rd and later reactions were performed by the same operation as in the 1st and 2nd reactions until the 12th time reaction where 600 hours were cumulatively passed from the start of 1st time reaction.

The oxidizing reaction results in 600 hours until the 12th time reaction were such that the conversion of diallyl ether was from 10.1 to 10.8 mol %, the selectivity of allyl glycidyl ether was from 89.0 to 90.5 mol %, the conversion of hydrogen peroxide was 95 to 99 mol %, and the amount of allyl glycidyl ether produced in the reaction time of 600 hours was 659 g. The reaction results are shown in Table 2.

TABLE 2

|  | Conversion of Diallyl Ether*1 (%) | Selectivity of Allyl Glycidyl Ether*2 (%) | Conversion of Hydrogen Peroxide*3 (%) | Time Used (hr) | AGE produced, g |
|---|---|---|---|---|---|
| Example 5*1 | 10.5 | 90 | 97 | 600 | 659 |
| Comparative Example 1*2 | 26.2 | 70 | 95 | 300 | 640 |

*1Conversion of diallyl ether: Diallyl ether consumed (mol)/raw material diallyl ether (mol) × 100 (%)
*2Selectivity of allyl glycidyl ether: Allyl glycidyl ether (mol)/{diallyl ether consumed (mol)} × 100 (mol %)
*3Conversion of hydrogen peroxide: Hydrogen peroxide consumed (mol)/raw material hydrogen peroxide (mol) × 100 (%)

The conversion of diallyl ether, the selectivity of allyl glycidyl ether and the conversion of hydrogen peroxide in Example 5 each is an average of 1st to 12th operations.

The conversion of diallyl ether, the selectivity of allyl glycidyl ether and the conversion of hydrogen peroxide in Comparative Example 1 each is an average of 1st to 6th operations.

Example 6

The catalyst used for 600 hours in Example 5 was heat-treated at 300° C. for 3 hours in an air atmosphere and 100 mg of the catalyst was added to a 20 ml-volume flask equipped with a thermometer, a reflux condenser and a magnetic stirrer. Then, 3.14 g (32.0 mmol) and 2.5 g of methanol were further added and the mixture was heated in a hot bath at 60° C. and vigorously stirred. Immediately after the temperature of the reaction mixture reached 57° C., 1.81 g (16.0 mmol as hydrogen peroxide) of an aqueous 30 wt % hydrogen peroxide solution was added to the system and by setting the reaction start time to this point, the stirring was continued until the passing of 30 minutes from the start of reaction. After the 30 minutes from the start of reaction, the reaction mixture was immediately cooled with ice to stop the reaction.

Thereafter, the reaction mixture was filtered to separate unreacted diallyl ether, unreacted hydrogen peroxide, water, product and solvent from the catalyst. At this time, the concentration of organic material in the obtained filtrate was analyzed by gas chromatography and the concentration of unreacted hydrogen peroxide was determined by potentiometric titration using Ce(IV). The reaction results are shown in Table 3. The conversion of diallyl ether was 19.2%, the selectivity of allyl glycidyl ether as the produced epoxy compound was 86.4% and the conversion of hydrogen peroxide was 54.1%. The reaction results are shown in Table 3.

TABLE 3

|  | Conversion of Diallyl Ether*1 (%) | Selectivity of Allyl Glycidyl Ether*2 (%) | Conversion of Hydrogen Peroxide*3 (%) | Yield of Allyl Glycidyl Ether*4 (%) |
|---|---|---|---|---|
| Example 6 | 19.2 | 86.4 | 54.1 | 33.2 |
| Comparative Example 2 | 16.3 | 87.0 | 44.3 | 29.9 |

*1Conversion of diallyl ether: Diallyl ether consumed (mol)/raw material diallyl ether (mol) × 100 (%)
*2Selectivity of allyl glycidyl ether: Allyl glycidyl ether (mol)/{diallyl ether consumed (mol)} × 100 (mol %)
*3Conversion of hydrogen peroxide: Hydrogen peroxide consumed (mol)/raw material hydrogen peroxide (mol) × 100 (%)
*4Yield of allyl glycidyl ether: Allyl glycidyl ether produced (mol)/{amount of raw material hydrogen peroxide (mol)} × 100 (%)

Example 7

The catalyst used for 600 hours in Example 5 was heat-treated at 300° C. for 3 hours in an air atmosphere and subjected to elementary analysis. The results are shown in Table 3. The titanium concentration in the catalyst was 2.1 wt % and the titanium/silicon molar ratio was 0.027. The results are shown in Table 4.

TABLE 4

|  | Titanium Concentration in Catalyst, mass % | Si/Ti*1 |
|---|---|---|
| Example 7 | 2.1 | 37 |
| Comparative Example 3 | 1.7 | 47 |

*1Molar ratio

Example 8

Production of Allyl Glycidyl Ether

An MFI-type titanosilicate catalyst (molar ratio of titanium and silicon: 0.0233) prepared in the same manner as in Reference Example was molded into a cylindrical pellet having a diameter of 3.0 mm and a height of 5.0 mm and 100.0 g of the pellet was filled in a glass-made reactor (diameter: 35 mm, height: 800 mm). The outside of the reaction tube was heated at 60° C. and to the mixer, diallyl ether was fed from Tank A at a flow rate of 7.0 g per hour, an aqueous 60 mass % hydrogen peroxide solution (hydrogen peroxide concentration: 60 mass %, water concentration: 40 mass %) was fed from Tank B at a flow rate of 4.15 g per hour, and a methanol solution of diallyl ether (diallyl ether concentration: 72 mass %, methanol concentration: 28 mass %) was fed from Tank C at a flow rate of 38.9 g per hour. A raw material mixture comprising diallyl ether: hydrogen peroxide: water: methanol=70.0:5.0:3.3:21.7 (by mass), obtained in the mixer, was fed from the bottom of the reactor at a flow rate of 50.0 g per hour for providing an LHSV (liquid space velocity) of 0.5 (/hour). The reaction mixture outflowed from the top of the reactor was passed through a condenser having a double tube structure and thereby cooled and then the reaction mixture was collected.

The concentration of organic material in the reaction mixture collected was analyzed, as a result, 6.92 g of allyl glycidyl ether was produced, the conversion of diallyl ether was 20.0 mol %, and the selectivity of allyl glycidyl ether based on diallyl ether was 85 mol %, per hour.

Subsequently, the reaction mixture collected was subjected to fractional distillation at atmospheric pressure and unreacted diallyl ether and methanol distilled out from the top were recovered. The recovered mixture of diallyl ether and methanol was analyzed, diallyl ether or methanol was supplied in a shortage portion so that the methanol solution of diallyl ether had a predetermined concentration (diallyl ether concentration: 72 mass %, methanol concentration: 28 mass %), and the solution was recycled to Tank C and again used for the reaction. The concentrated component which was not distilled out from the top in the fractional distillation was again distilled under reduced pressure of 13.3 kPa and allyl glycidyl ether was obtained from the top. This operation was repeated every one hour and the operation was performed 30 times in total until the passing of 30 hours from the start of first feeding of the raw material. The amount of diallyl ether consumed until the passing of 30 hours was 220 g and the amount of allyl glycidyl ether obtained was 199.3 g. The results in the reaction for 30 hours are shown in Table 5.

TABLE 5

| | Results at Outlet of Reactor | | Results of Reaction for 30 Hours | |
|---|---|---|---|---|
| | Conversion of Diallyl Ether*[1] (%) | Selectivity of Allyl Glycidyl Ether*[2] (%) | Amount of Diallyl Ether Consumed (g) | Amount of Allyl Glycidyl Ether Obtained (g) |
| Example 8 | 20 | 85 | 220 | 199.3 |
| Comparative Example 4 | 50 | 28 | 458 | 139.1 |

*[1]Conversion of diallyl ether: Diallyl ether consumed (mol)/raw material diallyl ether (mol) × 100 (%)
*[2]Selectivity of allyl glycidyl ether; Allyl glycidyl ether (mol)/{diallyl ether consumed (mol)} × 100 (mol %)

Comparative Example 1

Continuous Use Test Using Crystalline MFI-Type Titanosilicate

An MFI-type titanosilicate catalyst (molar ratio of titanium and silicon: 0.0233) prepared in the same manner as in Reference Example was molded into a cylindrical pellet having a diameter of 3.0 mm and a height of 7.0 mm and 15.0 g of the pellet was filled in a glass-made reactor (diameter: 35 mm, height: 300 mm). The outside of the reaction tube was heated at 60° C. and, from the bottom of the reaction tube, 25.0 g of a mixture of diallyl ether (concentration: 40.0 wt %), hydrogen peroxide (5.68 wt %), water (2.84 wt %) and methanol (51.48 wt %) was fed using a pump. The reaction solution outflowing for 1.0 hour from the start of reaction was collected, the organic material concentration was analyzed using gas chromatography and also the concentration of unreacted hydrogen peroxide was determined by potentiometric titration using Ce(IV). This operation was repeated for 50 hours and the reaction results during this time were recorded.

After 50 hours, the catalyst was taken out from the reaction tube and regenerated by performing a heating treatment at 300° C. for 3 hours in an air atmosphere. After the completion of regeneration treatment, the catalyst was cooled to 30° C. and again filled in the reaction tube and in the same manner as in the 1st time reaction, the reaction of the 2nd time was performed for 50 hours while recording the reaction results every one hour. Similarly to the first time reaction, this catalyst was taken out and regenerated by performing a heating treatment at 300° C. for 3 hours in an air atmosphere. The 3rd and later reactions were performed by the same operation as in the 1st and 2nd reactions until the 6th time reaction when 300 hours had cumulatively passed from the start of 1st time reaction.

The oxidizing reaction results in 300 hours until the 6th time reaction were such that the conversion of diallyl ether was from 25.5 to 26.1 mol %, the selectivity of allyl glycidyl ether was from 74.8 to 75.5 mol %, the conversion of hydrogen peroxide was 95.0 to 96.0 mol %, and the amount of allyl glycidyl ether produced in the reaction time of 300 hours was 640 g. The reaction results are shown in Table 2.

Comparative Example 2

The same operation as in Example 6 was performed except for using the catalyst used for 300 hours in Comparative Example 1. The results are shown in Table 3.

Comparative Example 3

The same operation as in Example 7 was performed except for using the catalyst used for 300 hours in Comparative Example 1. The results are shown in Table 4.

Comparative Example 4

An MFI-type titanosilicate catalyst (molar ratio of titanium and silicon: 0.0233) prepared in the same manner as in Reference Example was molded into a cylindrical pellet having a diameter of 3.0 mm and a height of 5.0 mm and 100.0 g of the pellet was filled in a glass-made reactor (diameter: 35 mm, height: 800 mm). The outside of the reaction tube was heated at 60° C. and to the mixer, diallyl ether was fed from Tank A at a flow rate of 15.0 g per hour, an aqueous 60 mass % hydrogen peroxide solution (hydrogen peroxide concentration: 60 mass %, water concentration: 40 mass %) was fed from Tank B at a flow rate of 9.15 g per hour, and a methanol solution of diallyl ether (diallyl ether concentration: 58 mass %, methanol concentration: 42 mass %) was fed from Tank C at a flow rate of 25.85 g per hour. A raw material mixture comprising diallyl ether: hydrogen peroxide: water: methanol=60.0:11.0:7.3:21.7 (by mass), obtained in the mixer, was fed from the bottom of the reactor at a flow rate of 50.0 g per hour where the LHSV was 0.5 (/hr). The reaction mixture outflowed from the top of the reactor was passed through a condenser having a double tube structure and thereby cooled and then the reaction mixture was collected.

The concentration of organic material in the reaction mixture collected was analyzed and as a result, 4.88 g of allyl glycidyl ether was produced, the conversion of diallyl ether was 50.0 mol %, and the selectivity of allyl glycidyl ether based on diallyl ether was 28 mol %, per hour.

Subsequently, the reaction mixture collected was subjected to fractional distillation in an atmospheric pressure and unreacted diallyl ether and methanol distilled out from the top were recovered. The recovered mixture of diallyl ether and methanol was analyzed, diallyl ether or methanol was supplied in a shortage portion so that the methanol solution of diallyl ether could have a predetermined concentration (diallyl ether concentration: 58 mass %, methanol concentration: 42 mass %), and the solution was recycled to Tank C and again used for the reaction. The concentrated component which was not distilled out from the top in the fractional distillation was again distilled under reduced pressure of 13.3 kPa and allyl glycidyl ether was obtained from the top. This operation was repeated every one hour and the operation was performed 30 times in total until the passing of 30 hours from the start of first feeding of the raw material. The amount of diallyl ether consumed until the passing of 30 hours was 458 g and the amount of allyl glycidyl ether obtained was 139.1 g. The results in the reaction for 30 hours are shown in Table 5.

INDUSTRIAL APPLICABILITY

As described in the foregoing pages, it is apparent that in the production of an oxidized compound of Compound A by using a peroxide as the oxidizing agent in the presence of a titanosilicate catalyst, a production process of suppressing the conversion of raw material Compound A to 50 mol % or less and aggressively performing recycling is very useful in view of the selectivity of the reaction.

The invention claimed is:

1. A process for producing allyl glycidyl ether, comprising the following first to third steps:
    First Step:
    a step of oxidizing a carbon-carbon double bond of diallyl ether using a peroxide as an oxidizing agent in the presence of a titanosilicate catalyst at a conversion of the diallyl ether of 30 mol % or less to obtain an oxidation reaction mixture;
    Second Step:
    a step of separating the diallyl ether from the oxidation reaction mixture obtained in the first step; and
    Third Step:
    a step of returning the diallyl ether obtained in the second step to the first step.

2. A process for producing allyl glycidyl ether according to claim 1, wherein the conversion of the diallyl ether in the first step is 15 mol % or less.

3. A process for producing allyl glycidyl ether according to claim 1 or 2, wherein the peroxide in the first step is a limiting reaction component, the peroxide concentration in the raw material mixture is from 0 to 50% by mass and the conversion of the peroxide is from 30 to 100 mol %.

4. A process for producing allyl glycidyl ether according to claim 3, wherein the conversion of the peroxide is from 80 to 100 mol %.

5. A process for producing allyl glycidyl ether according to claim 3, wherein the titanosilicate catalyst is at least one member selected from the group consisting of crystalline titanosilicate and meso-porous titanosilicate.

6. A process of producing allyl glycidyl ether according to claim 5, wherein the crystal structure of the crystalline titanosilicate is at least one member selected from the group consisting of MFI-type, AEL-type, EUO-type, FER-type, MEL-type, AFI-type, MWW-type, ATO-type, *BEA-type, MOR-type and -CLO-type, and the composition thereof is represented by the following compositional formula (1):

$$xTiO_2.(1-x)SiO_2 \qquad \text{Compositional Formula (1)}$$

(wherein x is from 0.0001 to 0.2).

7. A process for producing allyl glycidyl ether according to claim 5, wherein the oxidizing agent is at least one compound selected from the group consisting of hydrogen peroxide, tert-butyl hydroperoxide, tert-amyl hydroperoxide, cumene hydroperoxide, ethylbenzene hydroperoxide, cyclohexylhydroperoxide, methylcyclohexyl hydroperoxide, isobutylbenzene hydroperoxide, ethylnaphthalene hydroperoxide and peracetic acid.

8. A process for producing allyl glycidyl ether according to claim 7, wherein the oxidation reaction is performed in the presence of at least one solvent selected from the group consisting of alcohols, ketones, nitriles and water.

9. The process for producing an allyl glycidyl ether according to claim 1, wherein hydrogen peroxide is used as the oxidizing agent.

* * * * *